(12) United States Patent  (10) Patent No.: US 8,831,910 B2
Shintani et al.  (45) Date of Patent: Sep. 9, 2014

(54) METHOD OF MEASURING DEFECT DENSITY OF SINGLE CRYSTAL (75) Inventors: Yoshitomo Shintani, Toyota (JP); Katsuichi Kitagawa, Moriyama (JP)

(73) Assignee: Toyota Jidosha Kabushiki Kaisha, Aichi-ken (JP)

( * ) Notice: Subject to any disclaimer, the term of this patent is extended or adjusted under 35 U.S.C. 154(b) by 429 days.

(21) Appl. No.: 13/258,806

(22) PCT Filed: Mar. 10, 2010

(86) PCT No.: PCT/IB2010/000498
§ 371 (c)(1),
(2), (4) Date: Sep. 22, 2011

(87) PCT Pub. No.: WO2010/109285
PCT Pub. Date: Sep. 30, 2010

(65) Prior Publication Data
US 2012/0016630 A1  Jan. 19, 2012

(30) Foreign Application Priority Data
Mar. 24, 2009  (JP) .................. 2009-072340

(51) Int. Cl.
*G06F 15/00* (2006.01)
*G01B 5/18* (2006.01)
*G01B 7/26* (2006.01)
*G01B 11/22* (2006.01)
*H01L 21/66* (2006.01)
*G02B 21/00* (2006.01)
*G01N 21/95* (2006.01)
*G01N 21/88* (2006.01)

(52) U.S. Cl.
CPC ........ *G01N 21/9501* (2013.01); *G01N 21/9505* (2013.01); *H01L 22/24* (2013.01); *G01N 2021/8864* (2013.01); *G01N 2021/8896* (2013.01); *G01B 11/22* (2013.01); *G02B 21/0056* (2013.01); *G01N 2021/8874* (2013.01)
USPC ................ 702/166; 438/14; 438/17

(58) Field of Classification Search
CPC .............. G01B 11/22; G01N 21/9501; G01N 21/9505; G01N 2021/8864; G01N 2021/8874; G01N 2021/8896; G02B 21/0056; H01L 22/12; H01L 22/24
USPC ............... 702/34, 35, 97, 137, 155, 166, 170, 702/193; 382/145; 438/12, 14, 17, 459, 438/745; 428/141
See application file for complete search history.

(56) References Cited

U.S. PATENT DOCUMENTS 6,187,600 B1 * 2/2001 Fujisawa et al. ............... 438/14
6,197,606 B1 * 3/2001 Polignano et al. ............. 438/17
(Continued)

FOREIGN PATENT DOCUMENTS

JP  01-138449 A  5/1989
JP  03-003946 U  1/1991
(Continued)

OTHER PUBLICATIONS

International Search Report and Written Opinion for corresponding International Patent Application No. PCT/IB2010/000498 mailed Jun. 7, 2010.
(Continued)

*Primary Examiner* — John H Le
(74) *Attorney, Agent, or Firm* — Sughrue Mion, PLLC (57) ABSTRACT

A method of measuring the density of a plurality of defects that occur in a single crystal for each type of defect, includes: etching an observation surface, which is a surface of the single crystal, to form an etch pits at each defect; calculating the maximum depth, mean depth and depth curvature of each of etch pits formed at a plurality of defects present within a predetermined area on the observation surface; and comparing the measured maximum depth, mean depth and depth curvature with respective reference values to determine the type of each defect within the predetermined area.

8 Claims, 8 Drawing Sheets

(56) References Cited

U.S. PATENT DOCUMENTS

| | | |
|---|---|---|
| 6,803,240 B1 | 10/2004 | Bedell et al. |
| 2002/0188917 A1 | 12/2002 | Yokoyama et al. |
| 2004/0137752 A1 | 7/2004 | Sugamoto et al. |
| 2006/0281281 A1 | 12/2006 | Tanzawa et al. |

FOREIGN PATENT DOCUMENTS

| | | |
|---|---|---|
| JP | 08-008315 A | 1/1996 |
| JP | 09-021756 A | 1/1997 |
| JP | 09-199560 A | 7/1997 |
| JP | 09-246337 A | 9/1997 |
| JP | 2001-066122 A | 3/2001 |
| JP | 2001-068519 A | 3/2001 |
| JP | 2001-272340 A | 10/2001 |
| JP | 2006-147848 A | 6/2006 |
| JP | 2007-318031 A | 12/2007 |
| JP | 2008-028178 A | 2/2008 |

OTHER PUBLICATIONS

International Preliminary Report on Patentability for corresponding International Patent Application No. PCT/IB2010/000498 mailed Jun. 8, 2011.

* cited by examiner

| DISLOCATION IN 4H-SiC CRYSTAL | ORIENTATION OF DISLOCATION | BURGERS VECTOR |
|---|---|---|
| MICROPIPE (MP) | $\langle 0001 \rangle$ AXIS | $\langle 0001 \rangle$<br>$V = 3c, 4c,...$ |
| SCREW DISLOCATION (S OR D) | $\langle 0001 \rangle$ AXIS | $\langle 0001 \rangle$<br>$S(V = 1c), D(V = 2c)$ |
| EDGE DISLOCATION (E) | $\langle 0001 \rangle$ AXIS | $V = a/3 \langle 11-20 \rangle$ |
| BASAL PLANE DISLOCATION (B) | WITHIN (0001) PLANE | $V = a/3 \langle 11-20 \rangle$ |

METHOD OF MEASURING DEFECT DENSITY OF SINGLE CRYSTAL

BACKGROUND OF THE INVENTION

1. Field of the Invention

The invention relates to a method of measuring the defect density of a single crystal and, more particularly, to a method of measuring the defect density of a single crystal for each type of defect.

2. Description of the Related Art

A lattice defect of a semiconductor substrate or an epitaxial film on the semiconductor substrate influences the characteristic of an electronic device, such as a semiconductor device. Thus, the type and density of the defect are extremely important indices in terms of evaluation of quality of the substrate.

Various methods of measuring the defect density of a single crystal are described in the following documents.

Japanese Patent Application Publication No. 2007-318031 (JP-A-2007-318031) suggests that light (photoluminescence light, electroluminescence light, or the like) is irradiated to the inspection surface of an SiC substrate or epitaxial film to map the types and densities of lattice defects (dislocations such as edge dislocations, screw dislocations and basal plane dislocations (edge and screw), and stacking faults) present over the entire inspection surface. JP-A-2007-318031 describes that the types of lattice defects are determined through image analysis of the shapes of defects; however, it does not specifically describe on the basis of what image analysis criteria the acquired optical information is analyzed to determine the types of defects.

Japanese Patent Application Publication No. 2008-28178 (JP-A-2008-28178) suggests a substrate evaluation method that uses both alkali etching and anisotropic dry etching to detect the surface and internal dislocations of a substrate. Japanese Patent Application Publication No. 2001-66122 (JP-A-2001-66122) suggests a method that irradiates white light from a white light source to a measurement target surface and a reference surface while varying a relative distance between these two surfaces to change interference fringes to thereby measure the shape of the measurement target surface. Japanese Patent Application Publication No. 2001-68519 (JP-A-2001-68519) describes a method that separates an enlarged full-color image of an etched crystal face color by color to generate RGB (red, green and blue) color-separated images and then compares the color density of each pixel of each color-separated image with a reference color density to measure the density of etch pits (lattice defects). Japanese Patent Application Publication No. 2006-147848 (JP-A-2006-147848) describes that two-dimensional distribution evaluation of lattice structural defects of a semiconductor sample is conducted by a photoluminescence method in a nondestructive and noncontact manner. Japanese Patent Application Publication No. 8-8315 (JP-A-8-8315) describes a distribution map that is obtained in such a manner that a crystal face is divided by unit area into multiple sections and then the number of crystal dislocations in each unit area is counted.

However, none of the documents clearly describe a method of measuring the defect density for each type of defect.

In addition, Japanese Patent Application Publication No. 1-138449 (JP-A-1-138449) describes a method that converts an X-ray analysis intensity into the number of defects. Japanese Patent Publication No. 3-3946 describes a method that uses a photoacoustic spectroscopy device to measure an acoustic wave generated by expanding and contracting gas in contact with a sample using intermittently irradiated light. Japanese Patent Application Publication No. 9-21756 (JP-A-9-21756) describes a method that detects scattered light reflected on a semiconductor wafer surface layer to which a laser beam is irradiated and then detects surface layer defects from the scattered light image. Japanese Patent Application Publication No. 2001-272340 (JP-A-2001-272340) describes a method of measuring scattered light using data processing based on Rayleigh scattering.

However, none of the methods described in the above documents do not directly observe defects. Therefore, even when the number of defects may be read, it is difficult to separate defects type by type and count the defects for each type.

Furthermore, Japanese Patent Application Publication No. 9-199560 describes a method that measures the densities of various surface defects from an optical microscope image. However, the optical microscope image is two-dimensional information, so it is difficult to distinguish between foreign object and a defect.

Previously, a defect type has been determined through visual judgment within the field of vision of an optical microscope. The accuracy of this determination is at practical level; however, it costs too much work and time to conduct such judgment over a large area, such as a semiconductor wafer, so it is not practical.

Therefore, there is a need for a method of measuring defect densities, which is able to mechanically and accurately determine a defect type.

SUMMARY OF THE INVENTION

The invention provides a method of measuring defect densities, which is able to mechanically and efficiently determine the types of defects of a single crystal.

A first aspect of the invention relates to a method of measuring the density of a plurality of defects that occur in a single crystal by each type of defect. The method includes: etching an observation surface, which is a surface of the single crystal, to form an etch pit at each defect; calculating the maximum depth, mean depth and depth curvature of each of etch pits formed at a plurality of defects present within a predetermined area on the observation surface; and comparing the measured maximum depth, mean depth and depth curvature with respective reference values to determine the type of each defect within the predetermined area.

With the above configuration, the maximum depth, mean depth and depth curvature of each etch pit and the position of the center of gravity of the planar shape and maximum depth position of each etch pit may be mechanically measured by an interference microscope, a confocal laser scanning microscope, or the like. Thus, the measurement values may be automatically subjected to data processing to determine the type of defect for each defect by a computer incorporated in the microscope or an external computer. Therefore, it is possible to exceedingly efficiently measure the defect density for each type of defect over a large area, such as a semiconductor wafer, so it is highly practical.

The method according to the above aspect may further include: calculating the position of the center of gravity of a planar shape of each of the etch pits within the predetermined area; and calculating the maximum depth position of each of the etch pits formed within the predetermined area, wherein the type of each defect within the predetermined area may be determined on the basis of an orientation of the measured maximum depth position with respect to the calculated position of the center of gravity of the planar shape of each etch pit.

In the method according to the above aspect, the position of the center of gravity of the planar shape of each etch pit may be a geometrical center of gravity calculated from the contour of that etch pit on the observation surface.

The method according to the above aspect may further include binarizing a cross section perpendicular to a depth direction of each etch pit within the predetermined area to identify the etch pits.

In the method according to the above aspect, when a contour independent of an outer peripheral contour of the cross section of an etch pit within the predetermined area is present inside the outer peripheral contour of the etch pit, that etch pit may be identified as two etch pits.

In the method according to the above aspect, the maximum depth, mean depth and depth curvature may be measured by optical interferometry.

In the method according to the above aspect, the depth curvature of each etch pit may be a curvature of a cross section perpendicular to the observation surface or may be a curvature of a quadratic curve that is approximated to the cross section.

The method according to the above aspect may be performed over a plurality of the predetermined areas to map defect density distribution within an observation surface for each type of defect.

BRIEF DESCRIPTION OF THE DRAWINGS

The foregoing and further objects, features and advantages of the invention will become apparent from the following description of example embodiments with reference to the accompanying drawings, wherein like numerals are used to represent like elements and wherein.

DETAILED DESCRIPTION OF EMBODIMENTS

Hereinafter, an embodiment of the invention will be described in detail. In the following embodiment, an optimal etchant is used in correspondence with the type of a crystal to form etch pits. For an SIC single crystal, Melton KOH is used. For a GaAs single crystal, a mixed solution of $H_2SO_4$ and $H_2O_2$ is used. A crystal is immersed in these etchants to dissolve dislocation defects present on a crystal surface to form etch pits.

Three-dimensional shapes of etch pits are measured by an interference microscope as noncontact three-dimensional measurement using an interference microscope in the following embodiment.

The interference microscope irradiates white light to the surface of a sample and causes interference between reflected light from the surface of the sample and reflected light from a reference surface. When the objective lens of the interference microscope is moved in the vertical (height, etch-pit depth) direction, the amplitude of an interference waveform is maximal at a portion at which the distance of a sample optical path coincides with the distance of a reference surface optical path. A depth display resolution reaches 0.01 nm. The height on the surface of the sample is calculated from the peak position of the interference waveform. The same operation is carried out over all the pixels of a CCD camera. By so doing, the three-dimensional shape of the surface of the sample may be obtained within one field of view at a time. Through the above operation, depth information of a plurality of etch pits in one field of view may be obtained at a time.

First, a first embodiment will be described. The present embodiment used a sample such that an SiC film having a thickness of 10 µm was epitaxially grown on an SIC substrate (Si surface, off-angle of 8 degrees) by a CVD device.

A KOH reagent was put in a platinum melting pot, and was heated in an electric furnace with a thermoregulator. After checking that Melton KOHed by heat and then the temperature of the melt was stable at 490° C., a separately preheated sample was immersed in the melt using a platinum jig. The sample was taken out three minutes later and sufficiently washed by water. After that, the sample was dried and was observed by an optical microscope and an interference microscope.

Figure 1A:
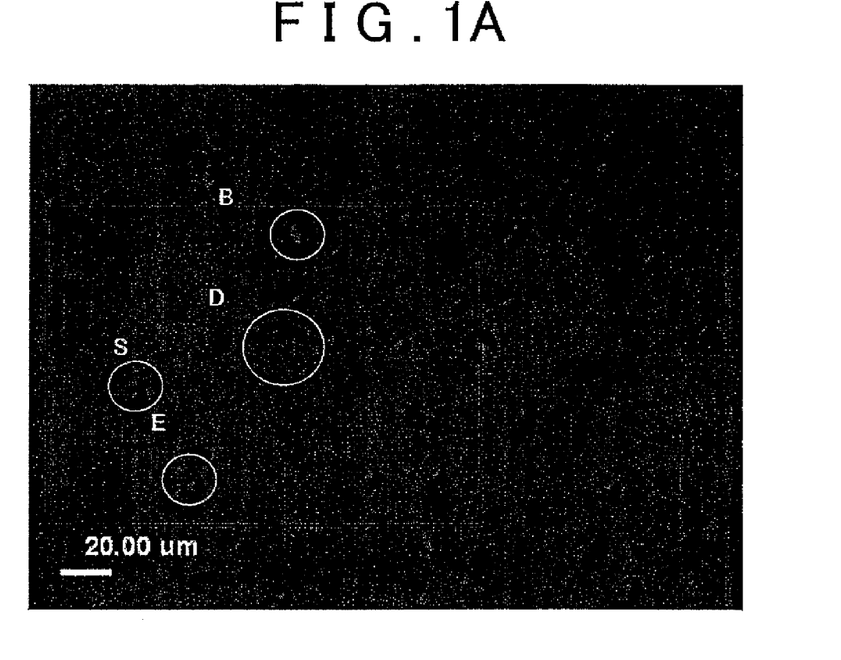
FIG. 1A and FIG. 1B are photos that respectively show the optical microscope image and interference microscope image of typical etch pits observed in an SiC epitaxial film on an SiC substrate.
Figure 1B:
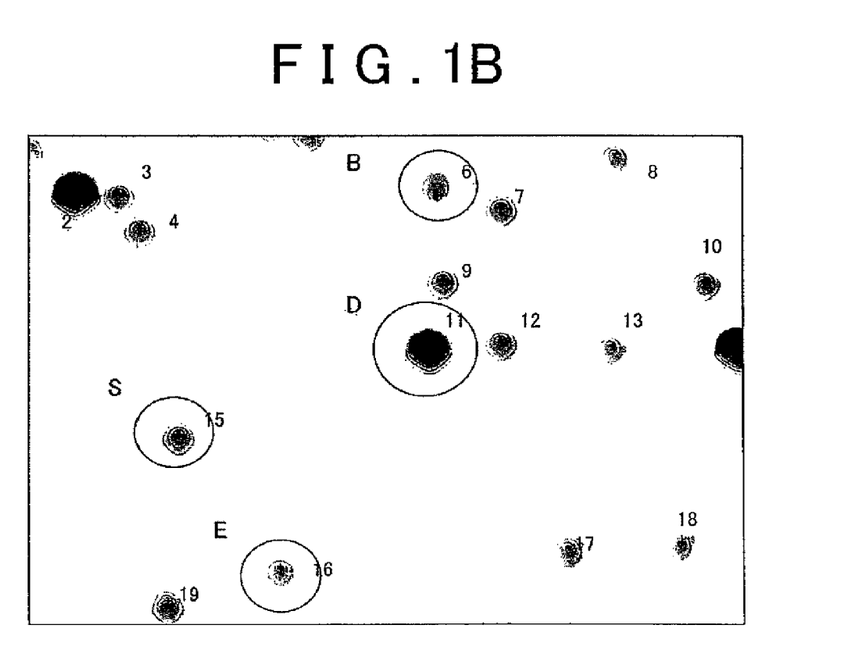

FIG. 1A shows an optical microscope image of typical etch pits. FIG. 1B shows an interference microscope image. FIG. 1B shows an image that is obtained by observing the area surrounded by the frame in FIG. 1A. The scaling factor was 50 times-fold magnification.

Figure 2A:
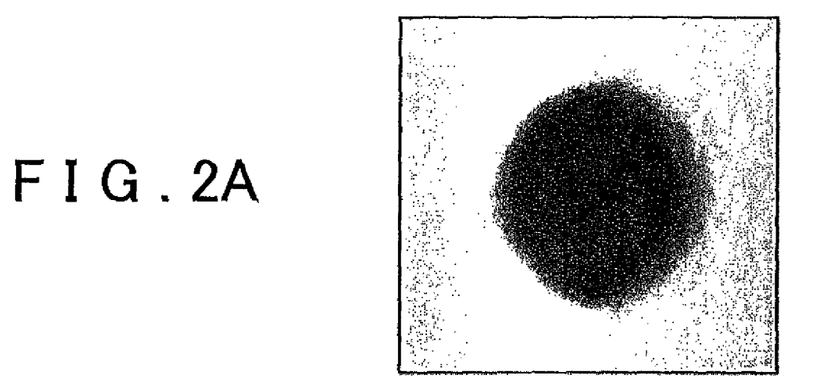
FIG. 2A, FIG. 2B and FIG. 2C are interference microscope photos that respectively show typical interference fringes that appear at respective etch pits of an edge dislocation, screw dislocation and basal plane dislocation.
Figure 2B:
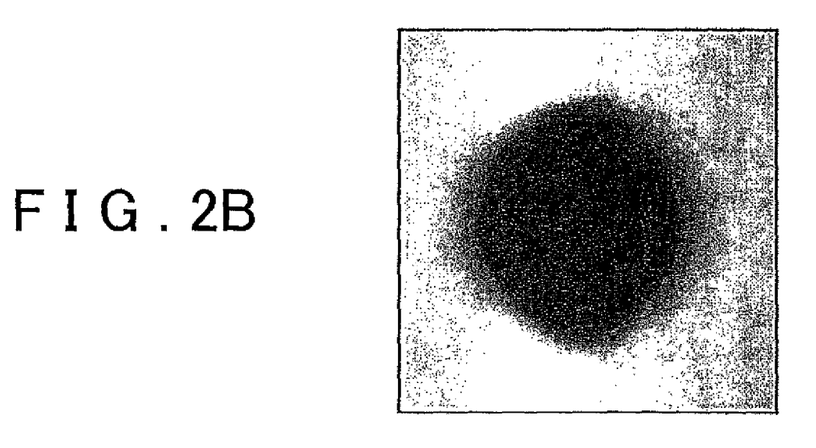
Figure 2C:
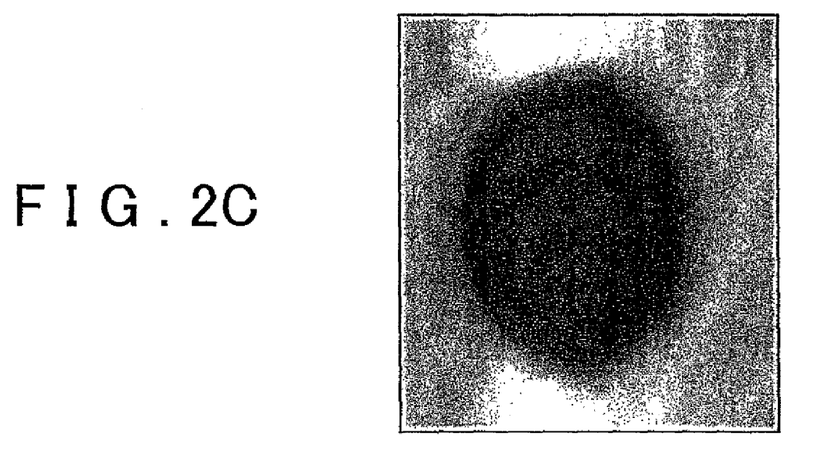

The interference fringes shown in FIG. 2A to FIG. 2C appear as annular contours surrounding respective maximum depth positions on the inner walls of the pits observed in FIG. 1B. FIG. 2A to FIG. 2C respectively show examples of observation of an edge dislocation, screw dislocation and basal plane dislocation. As shown in the drawings, dislocations may be classified into three types, that is, a group of A: edge dislocation and B: screw dislocation and C: basal plane dislocation. That is, the maximum depth position of a basal plane dislocation is offset toward an opposite side to those of the other dislocations. An edge dislocation and a screw dislocation are distinguished from each other by the size of dislocation. That is, a screw dislocation is larger than an edge dislocation.

Figure 3A:
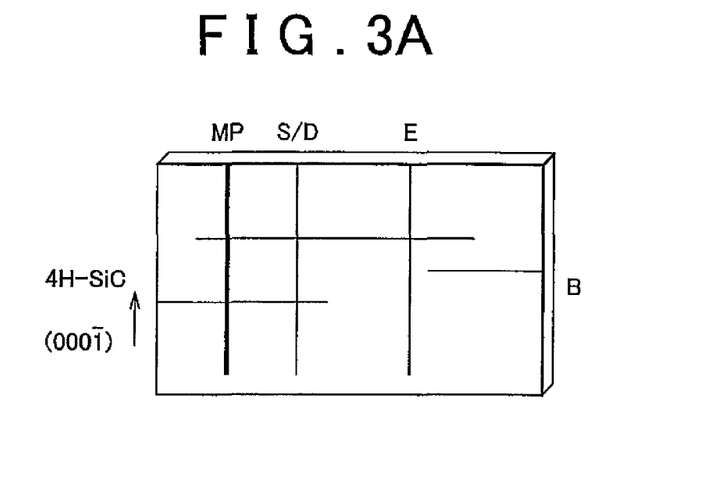
FIG. 3A is a schematic view that shows the orientation of each defect in an SiC single crystal.
Figure 3B:
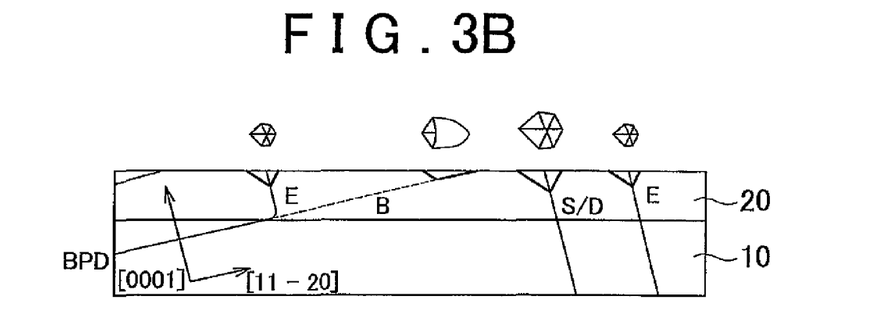
FIG. 3B is a schematic view that shows an CVD epitaxial film grown on an SiC single crystal substrate and various defects in the CVD epitaxial film and FIG. 3C is a table that collects the feature of each defect, for showing classification of defects.
Figure 3C:
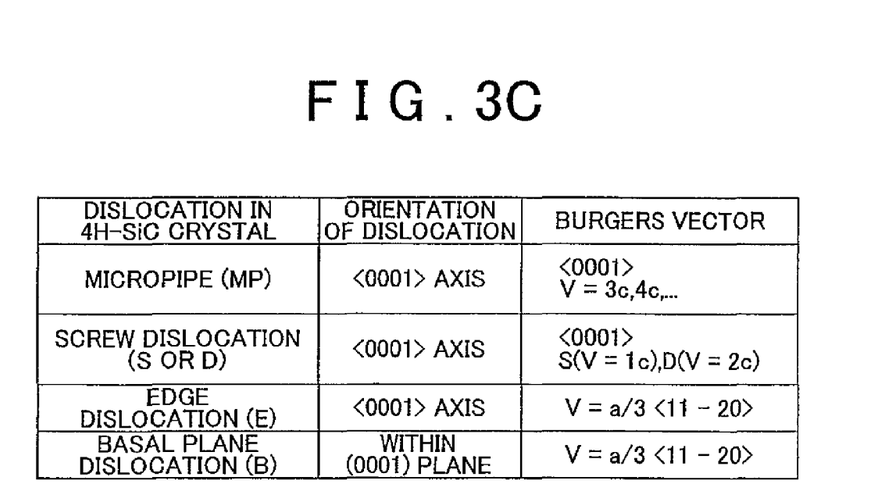

FIG. 3A to FIG. 3C show classification of crystal defects including a micropipe. FIG. 3A shows the orientation of each defect in a 4H—SiC crystal. FIG. 3B shows crystal defects in a 4H—SiC film 20 that is epitaxially grown on a 4H—SiC substrate (off-angle of 8 degrees) 10. FIG. 3C is a table that illustrates classified defects. The planar shapes of etch pits that appear on the surface of the epitaxial layer are schematically shown at the upper side in FIG. 3B.

A basal plane dislocation occurs so that a dislocation (a screw dislocation or an edge dislocation) in the SiC epitaxial film is reflected on the surface of the SiC substrate and then appears on the surface of the SiC film again. Although the classification of basal plane dislocation is different from the classification of screw dislocation and edge dislocation, the basal plane dislocation have a large adverse effect on the characteristic of the SiC single crystal. Therefore, the classification of basal plane dislocation is necessary and important on practical side. The maximum depth position is offset toward an opposite side from the other types of dislocations because of the above reflection, so the basal plane dislocation may be distinguished from the other types of dislocations.

Etch pits were visually classified within the field of view of the interference microscope. The etch pits were classified according to pit size into D, S and E, and were classified by the orientation of maximum depth position into B. These classifications correspond to D: screw dislocation (Burgers vector=2C), S: screw dislocation (Burgers vector=C), E: edge dislocation and B: basal plane dislocation.

Figure 4A:
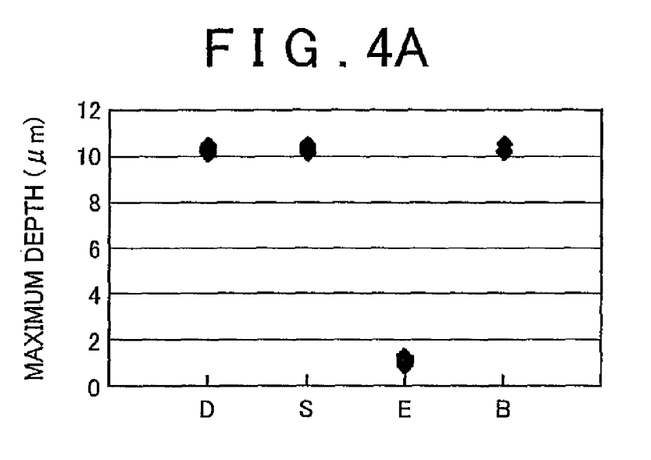
FIG. 4A, FIG. 4B and FIG. 4C are graphs that respectively plot the maximum depth, mean depth and depth curvature of each etch pit for each of defects (D, S, E, B) that are visually classified on the basis of the size and planar shape of the etch pit.
Figure 4B:
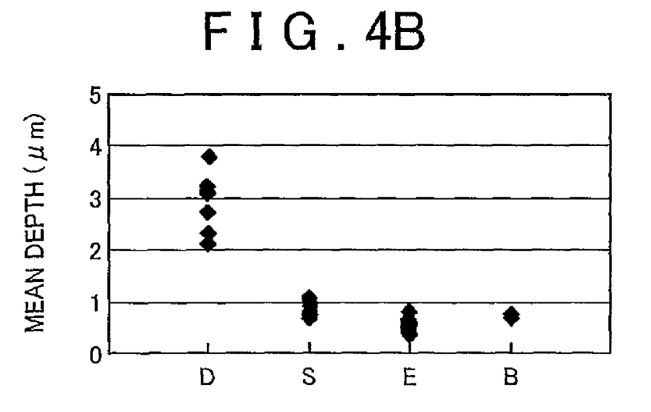
Figure 4C:
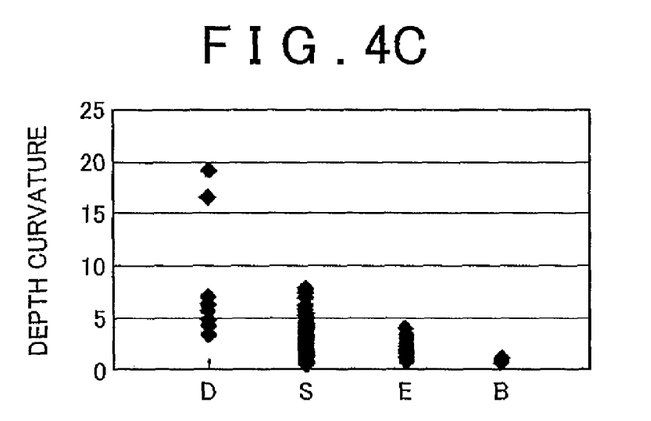

Seven fields of view of the same sample were measured, and the maximum depth, mean depth and depth curvature of each etch pit ware plotted in the graphs of FIG. 4A to FIG. 4C for each of the defects D, S, E and B visually classified on the basis of the size and planar shape of the etch pit. The results were collectively shown in Table 1.

TABLE 1

Measurement Results of Image Shown in FIG. 1B

| Defect Number | Defect | Maximum Depth [μm] | Mean Depth [μm] | Depth Curvature |
|---|---|---|---|---|
| 1 | — | — | — | — |
| 2 | D | 10.5 | 3.253 | 6.371 |
| 3 | S | 10.5 | 0.851 | 2.859 |
| 4 | S | 10.5 | 0.866 | 2.547 |
| 5 | — | — | — | — |
| 6 | B | 10.5 | 0.757 | 1.057 |
| 7 | S | 10.5 | 0.887 | 2.355 |
| 8 | E | 0.937 | 0.46 | 0.771 |
| 9 | S | 10.5 | 0.844 | 1.399 |
| 10 | S | 10.5 | 0.92 | 1.393 |
| 11 | D | 10.5 | 2.296 | 4.154 |
| 12 | S | 10.5 | 0.839 | 1.387 |
| 13 | E | 0.988 | 0.452 | 0.731 |
| 14 | — | — | — | — |
| 15 | S | 10.5 | 0.964 | 0.986 |
| 16 | E | 0.852 | 0.387 | 0.875 |
| 17 | S | 10.5 | 0.657 | 1.721 |
| 18 | E | 0.916 | 0.739 | 3.315 |
| 19 | S | 10.5 | 0.751 | 3.889 |

The defect E (edge dislocation) may be classified according to the maximum depth shown in FIG. 4A. The defect D or S (screw dislocation) may be classified according to the mean depth shown in FIG. 4B and the depth curvature shown in FIG. 4C. Defects other than the above may be classified as B (basal plane dislocation). The defects D and S both are screw dislocations; however, Burgers vector of D is 2, and Burgers vector of S is 1. Burgers vector of a micropipe is three or above, so no micropipe was identified in the sample.

The maximum depth, mean depth and depth curvature of each defect are determined as follows.

How to determine the maximum depth and the mean depth will be described. A histogram of the depths of all the pixels in the observation field of view of the sample is created, and a modal value is set as a reference depth. Here, the reference depth may be the depth of the surface of the etched SiC substrate.

A depth obtained by adding a threshold to the depth is used as a criterion for screening pixels, and only the pixels that meet the criterion are extracted.

By so doing, each etch pit is recognized as a group of discrete pixels.

The maximum depth and mean depth of each etch pit is calculated by the following mathematical expression.

(Maximum Depth)=(Maximum Value among Depths in Group of Pixels)−(Reference Depth)

(Mean Depth)=(Mean Value among Depths in Group of Pixels)−(Reference Depth)

Figure 5A:
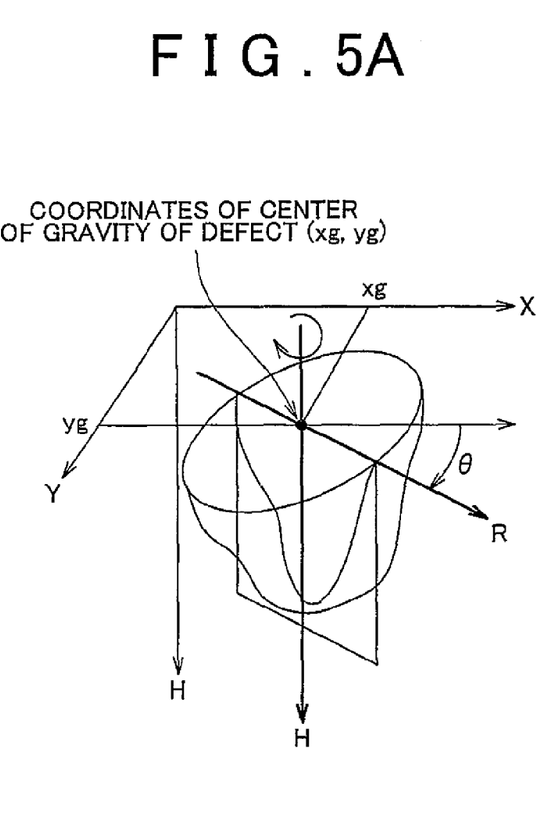
FIG. 5A and FIG. 5B are a plan view and cross-sectional view of an etch pit, respectively.
Figure 5B:
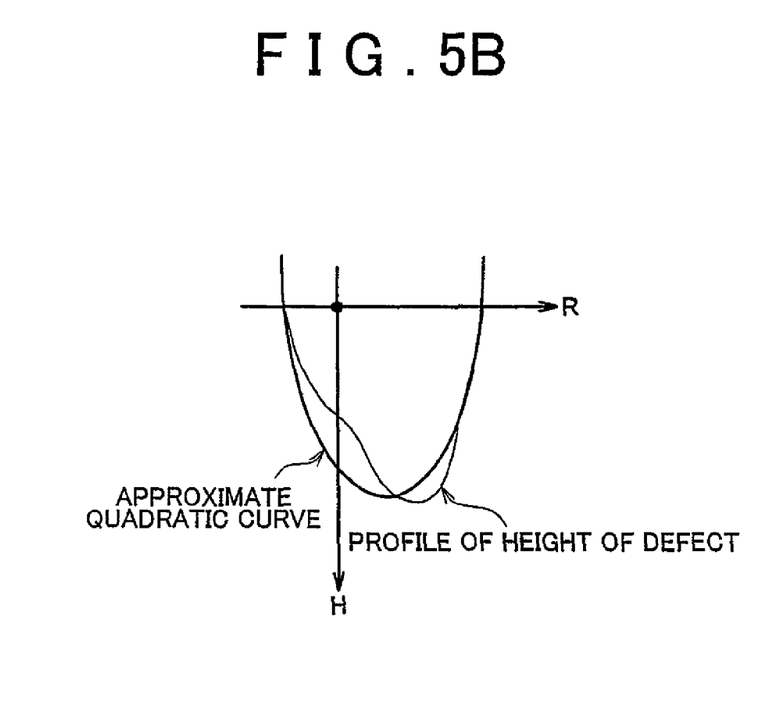

How to determine the depth curvature will be described with reference to FIG. 5A and FIG. 5B. As shown in FIG. 5A, the three-dimensional contour of an etch pit inner surface is approximated by a quadratic curve on the etch pit longitudinal section (plane parallel to the depth H, that is, plane perpendicular to the sample surface) that passes through the origin (xg, yg) as shown in FIG. 5B using the coordinate axis R on the sample surface and the coordinate axis H in the depth direction of the sample with the geometrical center of gravity (xg, yg) of the contour of the etch pit on the sample surface (X-Y plane) as the origin. Similar approximate curves of the second order are obtained for longitudinal sections at various angles of rotation θ about the origin (xg, yg). For example, when θ is shifted in π/4, approximate curves of the second order may be expressed as follows.

$$\theta j = (\pi/4)j (j=0,1,2) \quad (1)$$

$$H(R) = ajR^2 + bjR + c \quad (2)$$

The mathematical expression (2) may be transformed as follows.

$$H(R) = aj(R+\alpha)^2 + \beta \quad (2)'$$

Thus, a coefficient directly related to the curvature may be regarded as aj in the mathematical expression (2)'. Thus, the depth curvature ρ around the center of gravity (xg, yg) was used with the following definition.

$$\rho = \sum_{j=0}^{3} a_j$$

That is, the depth curvature ρ indicates "roundness" of a downward convex etch pit. As the coefficient aj increases, a portion around the vertex of the approximate quadratic curve gets sharper.

Furthermore, the offset of the maximum depth position (xMAX, yMAX) from the above obtained position of the center of gravity (xg, yg) may be used as one of important parameters. Particularly, a basal plane dislocation may be easily distinguished from the other types of dislocations on the basis of the orientation (sign) of the offset.

As illustrated in the present embodiment, defects may be not visually but mechanically classified according to magnitudes with respect to an appropriate reference value using the maximum depth, mean depth and depth curvature as parameters. The appropriate reference value may be, for example, the mean value, or the like, of each parameter.

The reference value of each parameter varies in accordance with the material and off-angle of a measured sample and etching conditions (reagent, temperature, time), so it is necessary to appropriately set the reference value on the basis of these conditions.

Next, a second embodiment will be described. The present embodiment used an SiC substrate (Si surface, off-angle of 8 degrees) as a sample.

A KOH reagent was used to etch the SiC substrate as in the case of the first embodiment. However, the etching temperature (Melton KOH temperature) was 410° C., and the etching time was an hour.

Figure 6A:
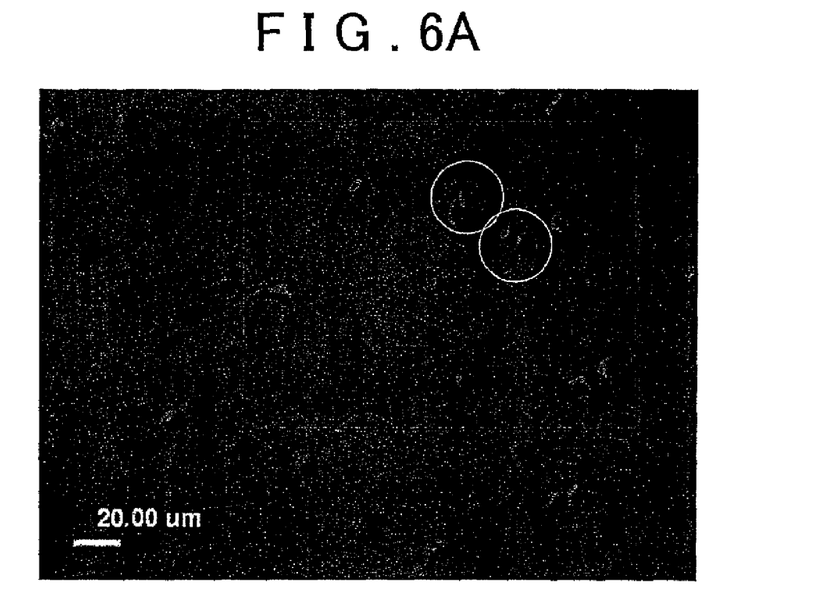
FIG. 6A and FIG. 6B are photos that respectively show the optical microscope image and interference microscope image of typical etch pits observed in an SiC substrate.
Figure 6B:
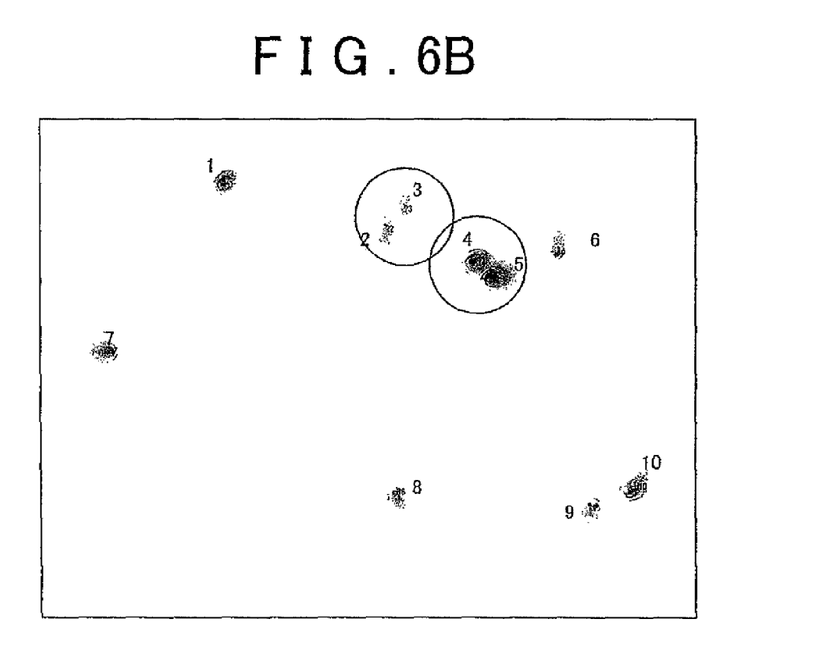

FIG. 6A shows an optical microscope image of typical etch pits. FIG. 6B shows an interference microscope image. FIG. 6B shows the area surrounded by the frame in FIG. 6A. The scaling factor was 50 times-fold magnification.

Overlapped two etch pits are observed at two portions in the optical microscope photo in FIG. 6A (a portion at which etch pits number 2 and 3 overlap each other, and a portion at which etch pits number 4 and 5 overlap each other).

As shown in FIG. 6B, even at each of these overlapped portions, two etch pits may be separated and visually observed by the interference microscope. The separation may be mechanically performed as follows.

Figure 7A:
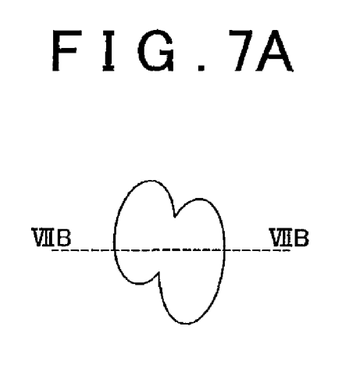
FIG. 7A and FIG. 7B are respectively a plan view and cross-sectional view that schematically show overlapped etch pits shown in FIG. 6B.
Figure 7B:
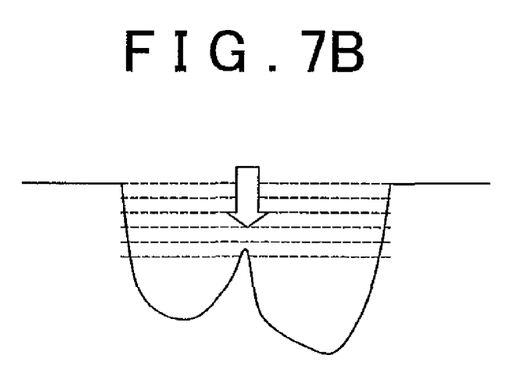

FIG. 7A schematically shows a plan view of the overlapped pits (number 2 and 3 or number 4 and 5). FIG. 7B schematically shows a longitudinal sectional view taken along the line VIIB-VIIB in FIG. 7A. As indicated by the plurality of broken lines in FIG. 7B, on data of the etch pits captured by the interference microscope, the etch pits are sliced at a plurality of different depths so as to form cross sections perpendicular to the depth direction, and, when a boundary remaining between the two etch pits, that is, a contour independent of the outer peripheral contour of the etch pits in a cross section, is detected inside the outer peripheral contour, two etch pits may be separately identified through binarization (determination as to whether there is a boundary). Through the above process, it is possible to further accurately count the number of defects, that is, to measure the defect density.

Then, when the offsets of the maximum depth positions with respect to the positions of the center of gravity of etch pits are used, the defects may be separated in further detail.

Figure 8:
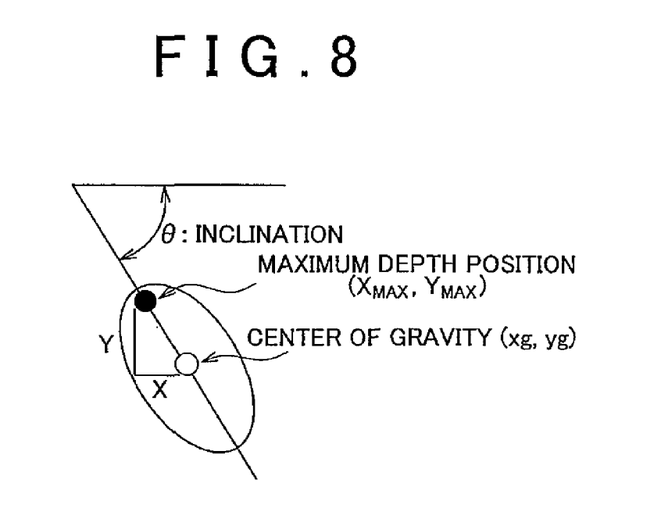
FIG. 8 is a schematic view that shows coordinate axes related to center of gravity and maximum depth position in a plan view of an etch pit.

FIG. 8 schematically shows the position of the center of gravity, the maximum depth position and the angle of a direction that connects the position of the center of gravity with the maximum depth position in the plan view of an etch pit on the sample surface. The maximum depth position of an etch pit corresponds to a dislocation core. A defect may be separated in further detail on the basis of the offset orientation angle of the maximum depth position with respect to the position of the center of gravity of an etch pit. The offset ($\Delta X$, $\Delta Y$) of the maximum depth position (xMAX, yMAX) with respect to the position of the center of gravity (xg, yg) is calculated as follows.

$$\Delta X = xMAX - xg$$

$$\Delta Y = yMAX - yg$$

$$\theta = \tan^{-1}(\Delta Y/\Delta X)$$

Table 2 collectively shows the classification results of all the etch pits shown in FIG. 6B. Particularly in this case, it appears that the offsets of the maximum depth positions of the etch pits are separated desirably.

TABLE 2

| Defect Number | Inclination [degree] | ΔX | ΔY | Maximum Depth [μm] | Mean Depth [μm] | Depth Curvature | Classification |
|---|---|---|---|---|---|---|---|
| 1 | 177.1 | − | − | 10.4 | 0.617 | 1.038 | A |
| 2 | 95.6 | − | − | 1.242 | 0.169 | 0.245 | B |
| 3 | 98.9 | − | − | 0.769 | 0.233 | 0.326 | B |
| 4 | 30.2 | − | + | 10.4 | 0.732 | 0.908 | A− |
| 5 | 5.7 | − | + | 10.4 | 0.753 | 0.832 | A− |
| 6 | 87.4 | + | − | 1.144 | 0.409 | 0.825 | C+ |
| 7 | 176.9 | + | + | 10.4 | 0.778 | 4.886 | A++ |
| 8 | 53.6 | − | + | 1.065 | 0.553 | 1.761 | C− |
| 9 | 143.6 | + | + | 1.304 | 0.225 | 0.386 | B++ |
| 10 | 125.2 | − | − | 10.4 | 0.618 | 1.862 | A |

Next, a third embodiment will be described. When defects may be classified as described above, a density distribution on a semiconductor wafer may be, for example, mapped for each type of defect.

Figure 9:
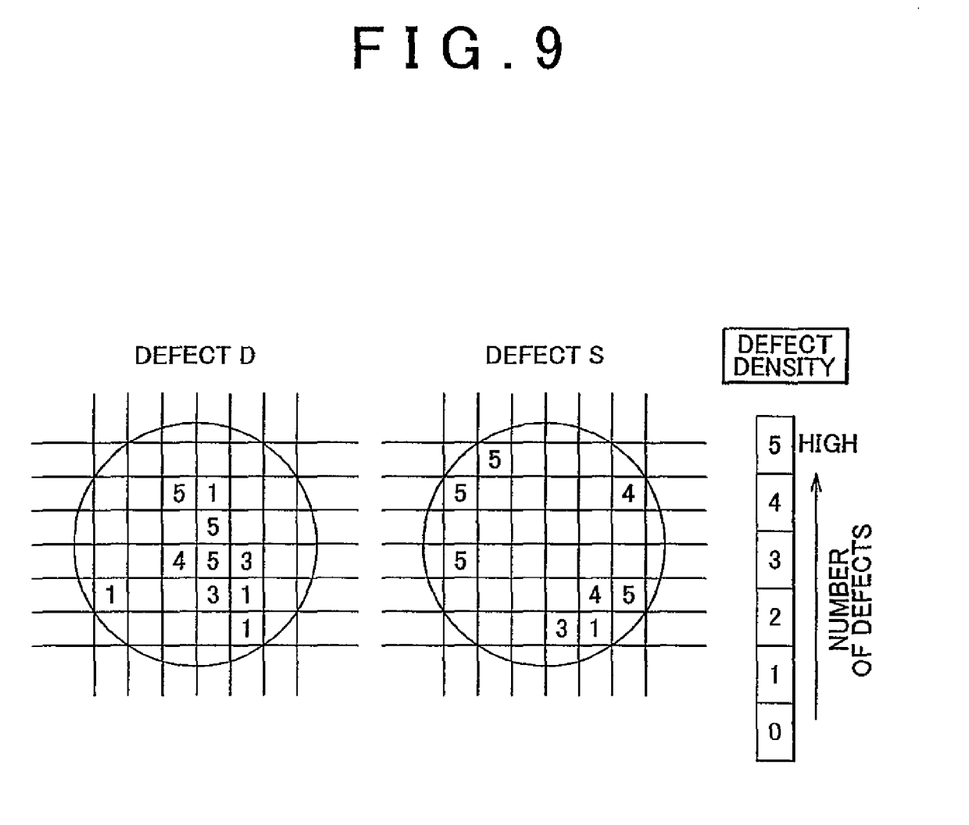
FIG. 9 is a schematic view that shows an example in which a mapped defect density distribution on a wafer.

In the example shown in FIG. 9, the defect density distribution of the screw dislocation D and the defect density distribution of the screw dislocation S are visualized on the same semiconductor wafer. When such defect density distribution information is fed back to a wafer manufacturing process, it becomes easy to improve manufacturing conditions for obtaining further high-quality wafers.

While some embodiments of the invention have been illustrated above, it is to be understood that the invention is not limited to details of the illustrated embodiments, but may be embodied with various changes, modifications or improvements, which may occur to those skilled in the art, without departing from the scope of the invention.

The invention claimed is:

1. A method of mechanically measuring the density of a plurality of defects that occur in a single crystal for each type of defect, comprising:
    etching an observation surface, which is a surface of the single crystal, to form an etch pit at each defect;
    calculating, using a microscope, the maximum depth, mean depth and depth curvature of each of etch pits formed at a plurality of defects present within a predetermined area on the observation surface; and
    comparing the measured maximum depth, mean depth and depth curvature with respective reference values to determine the type of each defect within the predetermined area, and
    calculating the position of the center of gravity of a planar shape of each of the etch pits within the predetermined area; and
    calculating the maximum depth position of each of the etch pits formed within the predetermined area, wherein the type of each defect within the predetermined area is determined on the basis of an orientation of the measured maximum depth position with respect to the calculated position of the center of gravity of the planar shape of each etch pit.

2. The method according to claim 1, wherein the position of the center of gravity of the planar shape of each etch pit is a geometrical center of gravity calculated from the contour of that etch pit on the observation surface.

3. The method according to claim 1, further comprising binarizing a cross section perpendicular to a depth direction of each etch pit within the predetermined area to identify the etch pits.

4. The method according to claim 3, wherein, when a contour independent of an outer peripheral contour of the cross section of an etch pit within the predetermined area is present inside the outer peripheral contour of the etch pit, that etch pit is identified as two etch pits.

5. The method according to claim 1, wherein the maximum depth, mean depth and depth curvature are measured by optical interferometry.

6. The method according to claim 1, wherein the depth curvature of each etch pit is a curvature of a cross section perpendicular to the observation surface.

7. The method according to claim 6, wherein the depth curvature of each etch pit is a curvature of a quadratic curve that is approximated to the cross section.

8. A method of mapping a defect density distribution within an observation surface for each type of defect, comprising performing the method according to claim 1 over a plurality of the predetermined areas.

* * * * *